United States Patent
Lin et al.

(10) Patent No.: US 12,303,539 B2
(45) Date of Patent: May 20, 2025

(54) METHOD OF USING LACTOBACILLUS FERMENTUM TCI757 FOR GAINING MUSCLE, PROMOTING SECRETION OF IRISIN, AND DECREASING VISCERAL FAT

(71) Applicant: TCI CO., LTD., Taipei (TW)

(72) Inventors: Yung-Hsiang Lin, Taipei (TW); Di Chang, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 18/047,658

(22) Filed: Oct. 19, 2022

(65) Prior Publication Data
US 2023/0285478 A1   Sep. 14, 2023

Related U.S. Application Data

(60) Provisional application No. 63/257,131, filed on Oct. 19, 2021.

(51) Int. Cl.
| | | |
|---|---|---|
| *A61K 35/747* | (2015.01) | |
| *A61K 9/00* | (2006.01) | |
| *A61P 3/04* | (2006.01) | |
| *A61P 21/00* | (2006.01) | |
| *C12N 1/20* | (2006.01) | |
| *C12R 1/225* | (2006.01) | |

(52) U.S. Cl.
CPC .......... *A61K 35/747* (2013.01); *A61K 9/0056* (2013.01); *A61P 3/04* (2018.01); *A61P 21/00* (2018.01); *C12N 1/205* (2021.05); *C12R 2001/225* (2021.05)

(58) Field of Classification Search
CPC ....... A61K 35/747; A61K 9/0056; A61P 3/04; A61P 21/00; C12N 1/205; C12R 2001/225
See application file for complete search history.

(56) References Cited

U.S. PATENT DOCUMENTS
2015/0343003 A1   12/2015   Kullisaar et al.
2019/0350223 A1*  11/2019   Leulier ................. A23K 10/18

FOREIGN PATENT DOCUMENTS
CN   112501046 A   3/2021
KR   20040064157 A   7/2004

OTHER PUBLICATIONS

Balakumar et al. (Improvement in glucose tolerance and insulin sensitivity by probiotic strains of Indian gut origin in high-fat diet-fed C57BL/6J mice, Eur J Nutr 57, 279-295 (2018), (Year: 2018).*
Nguyen (Adiponectin: Role in Physiology and Pathophysiology, Int J Prev Med 2020;11:136. (Year: 2020).*
Kwon et al. (Comprehensive amelioration of high-fat diet induced metabolic dysfunctions through activation of the PGC-1α pathway by probiotics treatment in mice, 2020, PLoS ONE 15(2):e0228932. (Year: 2020).*
Examination report dated Mar. 1, 2024, listed in correspondent China patent application No. 202211281183.X (publication No. CN 115989870 A).

* cited by examiner

*Primary Examiner* — Louise W Humphrey
*Assistant Examiner* — Alexander M Duryee
(74) *Attorney, Agent, or Firm* — Chieh-Mei Wang

(57) ABSTRACT

Lactobacillus fermentum is provided, where the Lactobacillus fermentum is Lactobacillus fermentum TCI757 and the Lactobacillus fermentum TCI757 was deposited at Deutsche Sammlung von Mikroorganismen und Zellkulturen under the accession number DSM 33914. A method of using Lactobacillus fermentum TCI757 of reducing fat and gaining muscle for a subject in need is also provided.

13 Claims, 7 Drawing Sheets
Specification includes a Sequence Listing.

METHOD OF USING LACTOBACILLUS FERMENTUM TCI757 FOR GAINING MUSCLE, PROMOTING SECRETION OF IRISIN, AND DECREASING VISCERAL FAT

CROSS-REFERENCE TO RELATED APPLICATION

This application claims the benefit of U.S. provisional application Ser. No. 63/257,131, filed on Oct. 19, 2021. The entirety of the above-mentioned patent application is hereby incorporated by reference herein and made a part of the specification.

REFERENCE OF AN ELECTRONIC SEQUENCE LISTING

The contents of the electronic sequence listing (P212558USI_ST26.xml; Size: 5,014 bytes; and Date of Creation: Feb. 1, 2024) is herein incorporated by reference in its entirety.

BACKGROUND

Technical Field

The present invention relates to Lactobacillus fermentum, and particularly to Lactobacillus fermentum TCI757, and use of the Lactobacillus fermentum or metabolites thereof in preparation of a composition for gaining muscle and reducing fat.

Related Art

Nowadays, various types of transportation are ramified in all directions, and lack of exercise or overeating is common in our lifestyle, which often causes modern people to be overweight.

Although awareness of attaching importance to exercise has gradually strengthened, how to increase muscle mass is still a goal pursued by many people within limited exercise time after busy work.

SUMMARY

In view of this, how to help the modern people more easily increase the muscle mass is an important goal of the inventor. The present invention provides a method of Lactobacillus fermentum TCI757 for gaining muscle and reducing fat, which includes administering to a subject in need thereof an effective dose of the Lactobacillus fermentum TCI757 or metabolites thereof.

In some embodiments, use of the Lactobacillus fermentum and/or metabolites thereof in preparation of a composition for gaining muscle and reducing fat are provided, the Lactobacillus fermentum is Lactobacillus fermentum TCI757 under the accession number of DSM 33914.

In some embodiments, the Lactobacillus fermentum TCI757 can inhibit myostatin.

In some embodiments, the Lactobacillus fermentum TCI757 can promote skeletal muscle cell expansion.

In some embodiments, the Lactobacillus fermentum TCI757 can promote secretion of irisin.

In some embodiments, the Lactobacillus fermentum TCI757 can promote secretion of adiponectin.

In some embodiments, the Lactobacillus fermentum TCI757 can inhibit fat accumulation.

In some embodiments, the Lactobacillus fermentum TCI757 can reduce body weight.

In some embodiments, the Lactobacillus fermentum TCI757 can reduce body fat weight.

In some embodiments, the Lactobacillus fermentum TCI757 can reduce visceral fat area.

In some embodiments, the Lactobacillus fermentum TCI757 can promote grip strength.

In some embodiments, an effective dose of the Lactobacillus fermentum TCI757 is 100 mg/day, and the content of the Lactobacillus fermentum is $10^9$ CFU/g.

In some embodiments, a food for gaining muscle and reducing fat is provided, which includes at least 100 mg of Lactobacillus fermentum TCI757 under the accession number of DSM 33914.

To sum up, the Lactobacillus fermentum TCI757 and metabolites thereof in any embodiment can inhibit myostatin, promote skeletal muscle cell expansion, promote secretion of irisin, promote secretion of adiponectin, inhibit fat accumulation, reduce body weight, reduce body fat weight, reduce visceral fat area, and improve grip strength, thereby achieving a purpose of gaining muscle and reducing fat.

DETAILED DESCRIPTION

Figures 1, 2:
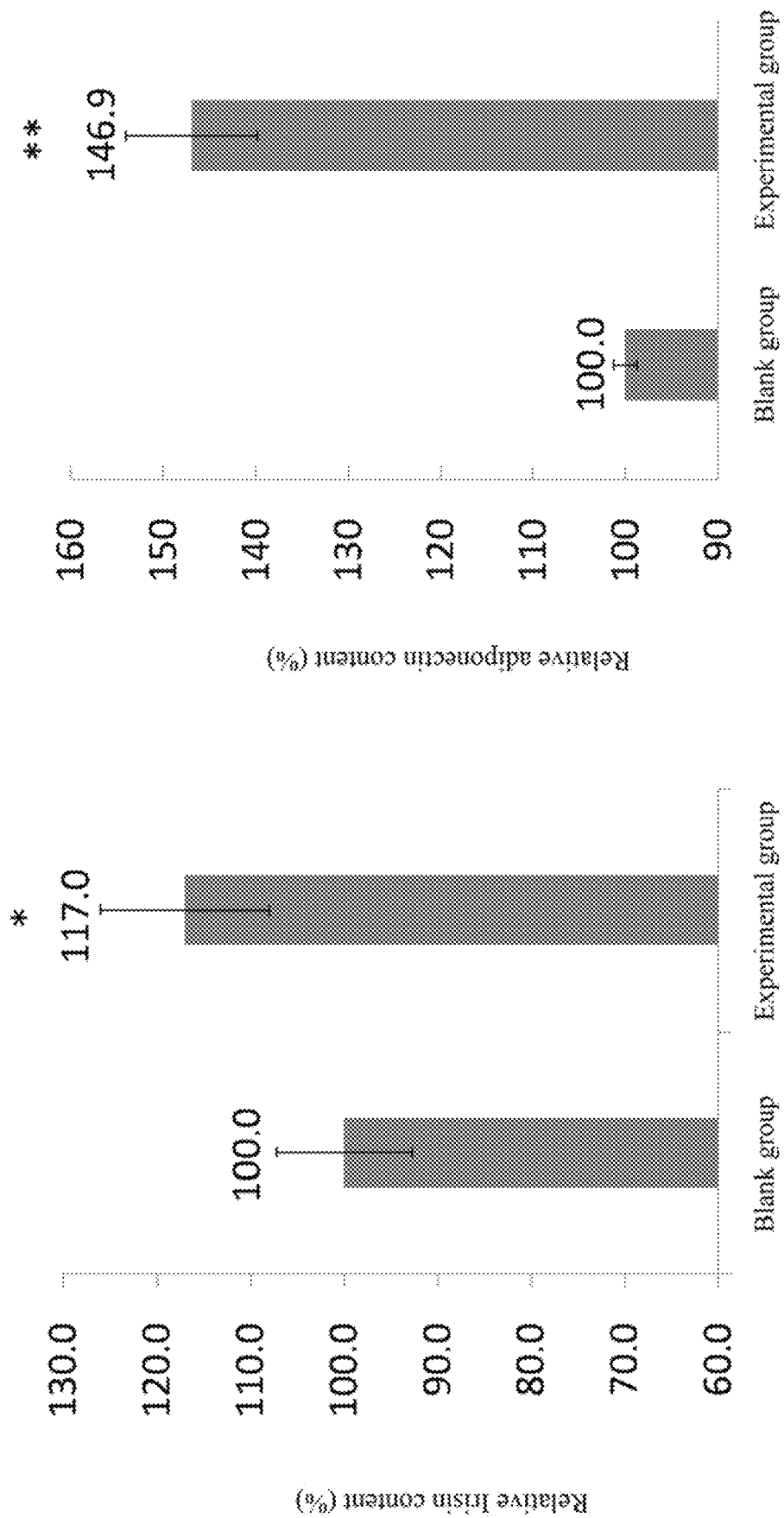
FIG. 1 is a result diagram of a test of Lactobacillus fermentum TCI757 in promoting secretion of Irisin.
FIG. 2 is a result diagram of a test of Lactobacillus fermentum TCI757 in promoting secretion of adiponectin.

Lactobacillus fermentum TCI757 is a strain isolated from Indonesian Tempeh. The Lactobacillus fermentum TCI757 was deposited at the Food Industry Research And Development Institute under the accession number BCRC 911064, and deposited at Deutsche Sammlung von Mikroorganismen und Zellkulturen under the accession number DSM 33914.

The Lactobacillus fermentum TCI757 is a gram-positive bacterium of Lactobacillus, belonging to a facultative anaerobe.

In some embodiments, use of the Lactobacillus fermentum TCI757 or metabolites thereof in preparation of a composition for gaining muscle and reducing fat is provided, the Lactobacillus fermentum TCI757 is Lactobacillus fermentum deposited at the Food Industry Research And Development Institute under the accession number BCRC 911064, and Lactobacillus fermentum deposited at Deutsche Sammlung von Mikroorganismen und Zellkulturen under the accession number DSM 33914.

In some embodiments, the Lactobacillus fermentum TCI757 can inhibit myostatin.

In some embodiments, the Lactobacillus fermentum TCI757 can promote skeletal muscle cell expansion.

In some embodiments, the Lactobacillus fermentum TCI757 can promote secretion of irisin.

In some embodiments, the Lactobacillus fermentum TCI757 can promote secretion of adiponectin.

In some embodiments, the Lactobacillus fermentum TCI757 can inhibit fat accumulation.

In some embodiments, the Lactobacillus fermentum TCI757 can reduce body weight.

In some embodiments, the Lactobacillus fermentum TCI757 can reduce body fat weight.

In some embodiments, the Lactobacillus fermentum TCI757 can reduce visceral fat area.

In some embodiments, the Lactobacillus fermentum TCI757 can promote grip strength.

In some embodiments, an effective dose of the Lactobacillus fermentum TCI757 is 100 mg/day, and the content of the Lactobacillus fermentum is 109 CFU/g.

In some embodiments, the aforementioned composition contains a specific amount of Lactobacillus fermentum TCI757 or metabolites thereof.

In some embodiments, the aforementioned composition may be a pharmaceutical. In other words, this pharmaceutical includes an effective dose of Lactobacillus fermentum TCI757 or metabolites thereof.

In some embodiments, the aforementioned pharmaceutical may be manufactured by using a technology known to those skilled in the art into dosage forms suitable for being enterally, parenterally, orally, or topically administrated.

In some embodiments, dosage forms for enteral or oral administration may be, but are not limited to, tablets, troches, lozenges, pills, capsules, dispersible powder or granules, solutions, suspensions, emulsions, syrup, elixirs, slurry or the like. In some embodiments, dosage forms for parenteral or local administration may be, but are not limited to, injections, sterile powder, external preparations or the like. In some embodiments, an administration method of the injection may be subcutaneous injection, intraepidermal injection, intradermal injection or intralesional injection.

In some embodiments, the aforementioned pharmaceutical may include a pharmaceutically acceptable carrier that is widely used in pharmaceutical manufacturing technologies. In some embodiments, the pharmaceutically acceptable carrier may be one or more of the following carriers: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome and the like. The type and number of a selected carrier falls within the scope of the professional literacy and routine technology of those skilled in the art. In some embodiments, the solvent used as the pharmaceutically acceptable carrier may be water, normal saline, phosphate buffered saline (PBS), or an aqueous solution containing alcohol.

In some embodiments, the aforementioned composition may include a food product, and the food product contains a specific amount of Lactobacillus fermentum TCI757 or metabolites thereof.

In some embodiments, the food product may be general foods, health foods or dietary supplements. In other words, the general foods, health foods or dietary supplements contain an effective dose of Lactobacillus fermentum TCI757 or metabolites thereof.

In some embodiments, the aforementioned food product may be manufactured by using a technology known to those skilled in the art into a dosage form suitable for oral administration. In some embodiments, the aforementioned general food may be a food product itself or a food additive of another food product. In some embodiments, the general foods may be, but are not limited to, beverages, fermented foods, bakery products or flavorings.

Example 1: Strain Identification

Firstly, an isolated strain isolated from the Tempeh was subjected to strain identification. A 16S ribosomal gene (16S rDNA) sequence (SEQ ID NO: 1) of the isolated strain was obtained by polymerase chain reaction (PCR). Subsequently, it could be seen from comparing the SEQ ID NO: 1 sequence with 16S ribosomal genes (16S rDNA) of other Lactobacillus fermentum (as shown in Table 1) on the website of the National Center for Biotechnology Information (NCBI) that the 16SrDNA sequence of the isolated strain was 98.78% identical to that of other Lactobacillus fermentum (as shown in Table 1). Therefore, the isolated strain was named Lactobacillus fermentum TCI757.

Here, the aforementioned Tempeh was purchased from Indonesia (Toko Indofamily Rui An, Product Name: KERIPIK TEMPE SAGU ORIGINAL). The Tempeh, also known as Danbei, is a traditional fermented food in Indonesia, which is made from soybeans. The Tempeh was prepared from raw soybeans by peeling, heating for thorough cooking and then fermenting.

TABLE 1

| Lactobacillus Fermentum | Identity (Per. Ident) |
| --- | --- |
| Lactobacillus fermentum strain HT4 16S ribosomal RNA gene, partial sequence | 98.78% |
| Lactobacillus fermentum strain 2951 16S ribosomal RNA gene, partial sequence | 98.78% |
| Lactobacillus fermentum strain 3715 16S ribosomal RNA gene, partial sequence | 98.78% |
| Lactobacillus fermentum strain 6879 16S ribosomal RNA gene, partial sequence | 98.78% |
| Lactobacillus fermentum strain 6336 16S ribosomal RNA gene, partial sequence | 98.78% |
| Lactobacillus fermentum strain 6020 16S ribosomal RNA gene, partial sequence | 98.78% |
| Lactobacillus fermentum strain 5561 16S ribosomal RNA gene, partial sequence | 98.78% |
| Lactobacillus fermentum strain HFB3 16S ribosomal RNA gene, partial sequence | 98.78% |

Example 2: Preservation and Cultivation Experiment of Lactobacillus fermentum TCI757

Firstly, the isolated Lactobacillus fermentum TCI757 was cultured in a liquid medium (MRS) to obtain a bacterial solution, and then the bacterial solution was mixed with glycerol at a ratio of 4:1. After this, the mixture of the bacterial solution and the glyceriol was stored at −80° C.

Next, the Lactobacillus fermentum TCI757 was inoculated into an MRS medium (BD Difco™ Lactobacilli MRS Broth, 1% (v/v)) with an inoculation amount of 1% (about $1\times10$ CFU/mL), and was cultured at 37° C. in an anaerobic environment for 18 h to form a TCI757 bacterial solution.

The Lactobacillus fermentum TCI757 bacterial solution was centrifuged at 5000 rpm for 5 min to obtain a supernatant, and the supernatant was filtered with a 0.2 m filter membrane, and the filtrate obtained was a TCI757 sample (that was, the TCI757 sample contained metabolites of the Lactobacillus fermentum TCI757).

Example 3: Irisin Secretion Promotion Test

Irisin is an exercise hormone secreted by human muscle during exercise, which can transform white fat into brown adipocytes, and promotes skeletal muscle expansion. The Irisin is derived from an FNDC5 gene, in a case of skeletal muscle exercise, the FNDC5 gene is prompted to translate an FNDC5 protein to hydrolyze to produce the Irisin.

3-1. Test Materials and Equipment Description:

Cell Line: mouse skeletal muscle cells (hereinafter referred to as C2C12 cells; purchased from ATCC®CRL-1772™)

Pretreatment Medium: Dulbecco's Modified Eagle Medium (DMEM) of 3.7 g/L of sodium bicarbonate, 10 vol % of FBS (Brand: Gibco) and 1 vol % of penicillin-streptomycin.

Treatment Medium: DMEM medium of 1 vol % of FBS and 1 vol % of horse serum.

ELISA Kit for Fibronectin Type III Domain Containing Protein 5 (FNDC5) (USCN; Cat. SEN576Mu).

3-2. Test Flows:

Here, the TCI757 sample cultivated in Example 2 was taken as a test sample. Whether the content of Irisin in the cells (FNDC5/irisin) was increased after the mouse muscle fiber cells C2C12 underwent test sample treatment was detected. Here, the experiment was conducted in three replicates.

Firstly, the mouse skeletal muscle cells were inoculated at a cell number of $1\times10^4$ cells/well into a 24-well plate containing 2 ml pretreatment medium per well, and were cultured at 37° C. until the cells formed a uniform single cell layer at the bottom of the culture plate of each well (i.e., the cell confluence reached 80%). Subsequently, the medium was replaced with the treatment medium for further culture of the C2C12 cells until the C2C12 cells differentiated and fused into multinucleated myotubes.

Next, the cells were divided into a blank group and an experimental group. No test sample was added in the blank group, and a sample to be tested at the concentration of 0.125% was added in the experimental group. Culture was performed for 48 hours to obtain a medium of each group.

Thereafter, 300 L/well of medium was taken from each group, and was placed in a 1.5 mL microcentrifuge tube. The microcentrifuge tube was then centrifuged at 10,000 g at 4° C. for 10 min, and the supernatant was collected.

The FNDC5/irisin content in cells in the supernatant was detected by the ELISA kit.

3-3. Test Result:

A student t-test was performed on the obtained results by using Excel software, so as to determine that there was a statistically significant difference between the two sample populations, as shown in FIG. 1 (in the figure, "*" represents that p value is less than 0.05, "" represents that p value is less than 0.01, and "*" represents that p value is less than 0.001. The more the "*", the significant the statistical difference).

See FIG. 1. Compared with the blank group (that was, its relative irisin content was regarded as 100%), the relative irisin content of the experimental group was 117%. In other words, the relative Irisin content of the experimental group was obviously increased by 17% with respect to the blank group. It can thus be seen that the Lactobacillus fermentum TCI757 effectively promoted muscle cells to secrete irisin. Thereby, conversion of the white fat into the brown fat was promoted, and heat-production metabolism of the fat was accelerated.

Example 4: Adiponectin Secretion Promotion Test

Adiponectin is a functional peptide secreted by adipocytes, which is related to maintaining the metabolic balance of glucose and lipids in vivo. Promotion of the adiponectin can reduce fat accumulation, promote the muscle cells to burn fat to be converted into energy, and further can prevent coronary artery diseases.

4-1. Test Materials and Equipment Description:

Cell Line: mouse bone marrow stromal cells (hereinafter referred to as OP9 cells) were used, and the OP9 cells were an OP9 cell line (ATCC CRL-2749) purchased from the American Type Culture Collection (ATCC®).

Medium: Minimum Essential Medium Alpha Medium cell medium (purchased from Gibco, USA, Cat. 12000-022) was used as a substrate, added with 20% of fetal bovine serum (purchased from Gibco, USA, Cat #10437-028), and 0.1% of antibiotic (Antibiotic-Antimycotic, purchased from Gibco, USA, Cat. 15240-062).

Detection was performed with an adiponectin detection reagent kit (purchased from CUSABIO, Model: CSB-E07272m).

4-2. Test Flows:

Here, the TCI757 sample cultivated in Example 2 was taken as a test sample. Whether the content of adiponectin in the cells was increased after the differentiated adipocytes underwent test sample treatment was detected. Here, the experiment was conducted in three replicates.

A 24-well culture plate was taken, $8\times10^4$ OP9 cells and 500 µL of the aforementioned medium were inoculated into each well, and the culture plate was placed in a carbon dioxide incubator for culture at 37° C. for 7 days. During the 7-day cell culture, the medium was replaced every 3 days. After 7 days, formation of lipid droplets in the cells was observed under a microscope (magnification: 400×) to confirm that the cells had completely differentiated into the adipocytes.

Then, the differentiated adipocytes were divided into the following two groups: a blank group and an experimental group. No test sample was added in the blank group, and a sample to be tested at the concentration of 0.25% was added in the experimental group. Culture was performed for 48 h to obtain a medium of each group.

After 24 h of culture at 37° C., the medium in the well was transferred into a 1.5 mL microcentrifuge tube. The microcentrifuge tube was centrifuged at 1000×g at 2° C. to 8° C. for 15 min. The centrifuged supernatant was transferred into a new 1.5 mL microcentrifuge tube. Subsequently, the supernatant was diluted by 2000 folds. Subsequently, detection was performed with the adiponectin detection reagent kit.

Finally, an OD548 nm read-out value of each group was read with an ELISA reader (BioTek) (the larger the O.D. value, the higher the content of adiponectin). When the adiponectin content of the blank group was 100%, the adiponectin content of the experimental group was converted, after comparative conversion of absorbance values and multiplication by a dilution fold, as shown in FIG. 2.

4-3. Test Result:

A student t-test was performed on the obtained results by using Excel software, so as to determine that there was a statistically significant difference between the two sample populations, as shown in FIG. 2 (in the figure, "*" represents that p value is less than 0.05, "" represents that p value is less than 0.01, and "*" represents that p value is less than 0.001. The more the "*", the significant the statistical difference).

See FIG. 2. Compared with the blank group (that was, its relative adiponectin content was regarded as 100%), the relative adiponectin content of the experimental group was 146.9%. In other words, the relative adiponectin content of the experimental group was obviously increased by 46.9% with respect to the blank group. It can thus be seen that the Lactobacillus fermentum TCI757 effectively promoted the adipocytes to secrete the adiponectin. Thereby, the conversion of the white fat into the brown fat was promoted, and the heat-production metabolism of fat was accelerated. The Lactobacillus fermentum TCI757 strain of the present invention has a potential to effectively increase the adiponectin content and reduce fat.

Example 5: Lipid Droplet Accumulation Test

Fat was stored in the adipocytes in the form of lipid droplets. Based on this, stained lipid droplets were analyzed in this test to observe the number of lipid droplets in the cells, so as to confirm a state of fat accumulation. Subsequently, a stain was then dissolved out and analyzed as a quantitative numerical index.

5-1. Test Materials and Equipment Description:

Cell Line: mouse bone marrow stromal cells (hereinafter referred to as OP9 cells) were used, and the OP9 cells were an OP9 cell line (ATCC CRL-2749) purchased from the American Type Culture Collection (ATCC®).

Pre-adipocyte expansion medium: Minimum Essential Medium Alpha (MEMα, Brand: Gibco) added with 20 vol % of FBS (Brand: Gibco) and 1 vol % of penicillin-streptomycin.

Differentiation Medium Used: MEMα added with 20 vol % of FBS (Brand: Gibco) and 1 vol % of penicillin-streptomycin (Brand: Gibco).

Stock Solution of Oil-Red O Staining Reagent: The oil-red O staining reagent (Brand: Sigma) was thoroughly dissolved in 100% isopropanol (Supplier: ECHO) to prepare 3 mg/mL stock solution of the oil-red O staining reagent. To obtain an oil-red O working solution available for use, the stock solution of oil-red O staining reagent was immediately diluted with secondary water (ddH$_2$O) to a concentration of 1.8 mg/mL before use, so as to obtain 60% stock solution of the oil-red O staining reagent.

Microscope (Brand: zeiss), and ELISA Reader (Brand: BioTek)

5-2. Test Flows:

Firstly, the OP9 cells were inoculated with a cell number of 8×10$^4$ cells/well into each well of a 24-well culture plate containing 500 µL pre-adipocyte expansion medium, and the culture plate was cultured at 37° C. for 7 days. During the 7-day culture, a fresh 500 µL differentiation medium was replaced every 3 days. After the 7-day culture, the formation of lipid droplets in the cells in each well was observed under the microscope (Brand: ZEISS) to confirm that the cells had completely differentiated into the adipocytes for subsequent experiments.

Experimental Group: The TCI757 sample cultivated in Example 2 was taken as a test sample, with 62.5 µL contained in 500 µL medium per well (i.e., the concentration was 0.125%), and the test sample was added into the differentiation medium, and was cultured at 37° C. for 7 days. The medium was replaced every 3 days during the 7-day cell treatment.

Blank Group: no treatment was made, that was, culture was performed at 37° C. for 7 days, without adding other compounds to the differentiation medium containing the differentiated adipocytes. During the 7-day cell treatment, the medium was replaced every 3 days.

Figure 3:
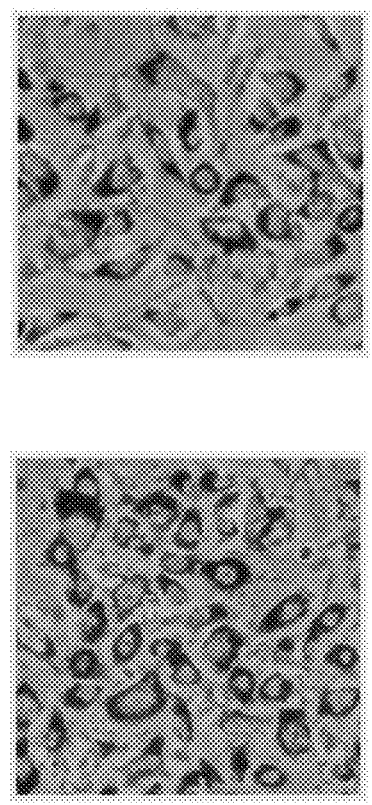
FIG. 3 is a cell state diagram of a test of Lactobacillus fermentum TCI757 in inhibiting fat accumulation.

Subsequently, staining with oil-red O was performed according to the following steps. After the 7-day cell treatment, the medium was removed. The adipocytes were washed with 1 mL of phosphate buffered saline (PBS) twice. 1 mL of 10% formaldehyde was then added and reacted at room temperature for 30 min to fix the adipocytes. Subsequently, after the formaldehyde was removed, the adipocytes were gently washed twice with 1 mL PBS. Subsequently, 1 mL of 60% isopropanol was added to the cells in each well, and reacted for 1 min. Then, the isopropanol was removed and 1 mL of oil-red O working solution was added to react with the adipocytes at room temperature for 1 h. Subsequently, the oil-red O working solution reacted with the adipocytes was removed, and the adipocytes were quickly decolorized with 1 mL of 60% isopropanol for 5 s. The cells were observed and photographed under the microscope (magnification: 400×). The results are shown in FIG. 3.

Thereafter, the stained groups were then quantified for red-oil O according to the following steps. 100% isopropanol was added into each well, and the culture plate was placed on a shaker to react for 10 min to dissolve the lipid droplets. Then, 100 µL of the aforementioned solution was taken from each well and transferred to a 96-well culture plate, and an absorbance value (OD510 nm) of each well was read with the ELISA reader at a wavelength of 510 nm.

Figure 4:
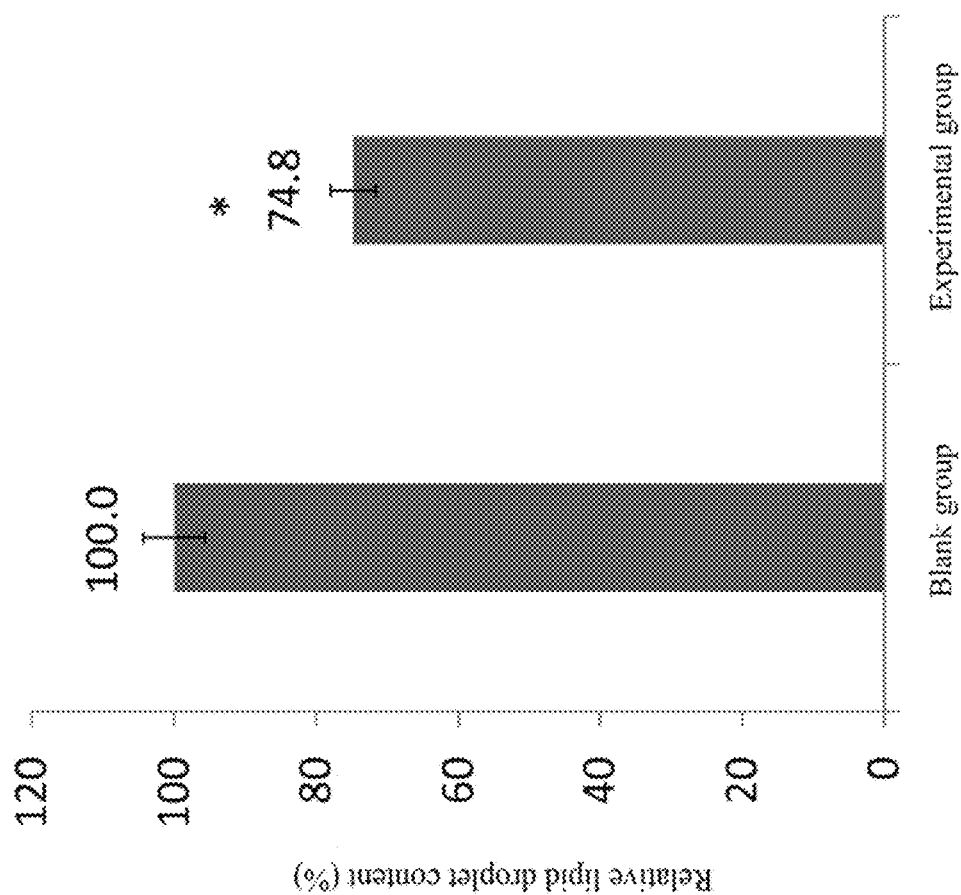
FIG. 4 is a result diagram of a test of Lactobacillus fermentum TCI757 in inhibiting fat accumulation.

After measurement, the lipid droplet accumulation (%) was worked out by substituting the measured absorbance value into the following formula I. In other words, the lipid droplet accumulation (%) of each group was calculated with the lipid droplet accumulation of the blank group being regarded as 100%. The conversion results are shown in FIG. 4.

$$\text{Lipid Droplet Accumulation (\%)} = (OD_{510} \text{ sample}/OD_{510} \text{ control}) \times 100\% \quad (1) \text{ formula I.}$$

The OD$_{510}$ sample represents an absorbance value of a group to be converted, and the OD$_{510}$ control represents an absorbance value of the blank group.

5-3. Test Result:

See FIG. 3. It could be observed from the cells of the blank group that the number of red (dark) lipid droplets in the cells of the blank group was significantly more than that of the experimental group, and a cell size was also larger. It can be seen that the Lactobacillus fermentum TCI757 effectively inhibited the size of the adipocyte, thereby achieving a function of losing weight.

See FIG. 4. In a case where the lipid droplet accumulation of the blank group was 100%, the lipid droplet accumulation of the experimental group was only 74.8%. It can thus be seen that the Lactobacillus fermentum TCI757 effectively inhibited fat accumulation and reduced fat formation of a subject, thereby achieving the function of losing weight.

Example 6: Myostatin Gene Expression Test

Satellite cells can be activated by inhibiting myostatin (MSTN) to increase muscle regeneration.

6-1. Test Materials and Equipment Description:

Cell Line: mouse skeletal muscle cells (hereinafter referred to as C2C12 cells; purchased from ATCC®CRL-1772™)

Medium: Dulbecco's Modified Eagle's Medium (DMEM, purchased from Gibco, Product Number: 12800017) was used as a substrate, added with 10% of fetal bovine serum (FBS, purchased from Gibco, Product Number: 10437-028) and 1% of antibiotic (purchased from Gibco, Product Number: 15240-062).

10× DPBS Dulbecco's Phosphate Buffered Saline (purchased from Gibco; Cat. 14200-075).

RIPA Pyrolysis and Extraction Buffer (Thermo, Product Number #89900).

6-2. Test Flows:

Firstly, a 6-well culture plate was taken, each well was inoculated with 1×10⁶ C2C12 cells and 2 mL medium, and the culture plate was cultured overnight. The cultured C2C12 cells were divided into three groups: a blank group, a control group and an experimental group.

Blank Group: Only a medium was added, and then was cultured at 37° C. for 24 h.

Control Group: 0.25% of MRSD was added, the MRSD referring to a blank medium during bacteria culture.

Experimental Group: 0.25% of the TCI757 sample prepared in Example 2 was added, and then was cultured at 37° C. for 24 h.

The cultured cells in each group were centrifuged at 400×g for 5 min, and then, the supernatant was removed. Remaining cells were washed with the 1× DPBS buffer and then were centrifuged at 400×g for 5 min again. The supernatant was removed, and then, 500 L of the RIPA pyrolysis and extraction buffer was added to pyrolyse cytomembranes to form cell solutions, respectively.

Subsequently, RNA in cell solutions in the two groups was collected by using an RNA extraction reagent kit (purchased from Geneaid, Taiwan, Lot No. FC24015-G). Subsequently, 1000 nanograms (ng) of the RNA extracted from each group was taken as a template, and reverse transcription was performed by SuperScript® III reverse transcriptase (purchased from Invitrogene, USA, No. 18080-051) with primer annealing to produce corresponding cDNA. Thereafter, quantitative real-time reverse transcription polymerase chain reaction was performed on products underwent inverse transcription in the two groups with the following primers by using ABI StepOnePlus™ Real-Time PCR system (Thermo Fisher Scientific, USA) and KAPA SYBR FAST (purchased from Sigma, USA, No. 38220000000) to observe the expression quantity of genes of PBMC cells in the experimental group and the control group. Instrument setting conditions of the quantitative real-time reverse transcription polymerase chain reaction were as follows: reaction for 1 s at 95° C., reaction for 20 s at 60° C., 40 circles in total, and gene quantification was performed using a 2-ΔCt method. Here, the quantitative real-time reverse transcription polymerase chain reaction performed with cDNA can indirectly quantify the mRNA expression quantity of each gene, thereby inferring the expression quantity of a protein encoded by each gene, as shown in FIG. 5.

Target Gene MSTN, the primers used included: a primer named as MSTN-F, sequence No.: SEQ ID NO: 2, sequence: TTCCGGTTCCCTTTTCCCTT, and length: 577 bp; and a primer named as MSTN-R, sequence No.: SEQ ID NO: 3, sequence: TCTGCAGCTTGTGTTGCTCT, and length: 577 bp.

Figure 5:
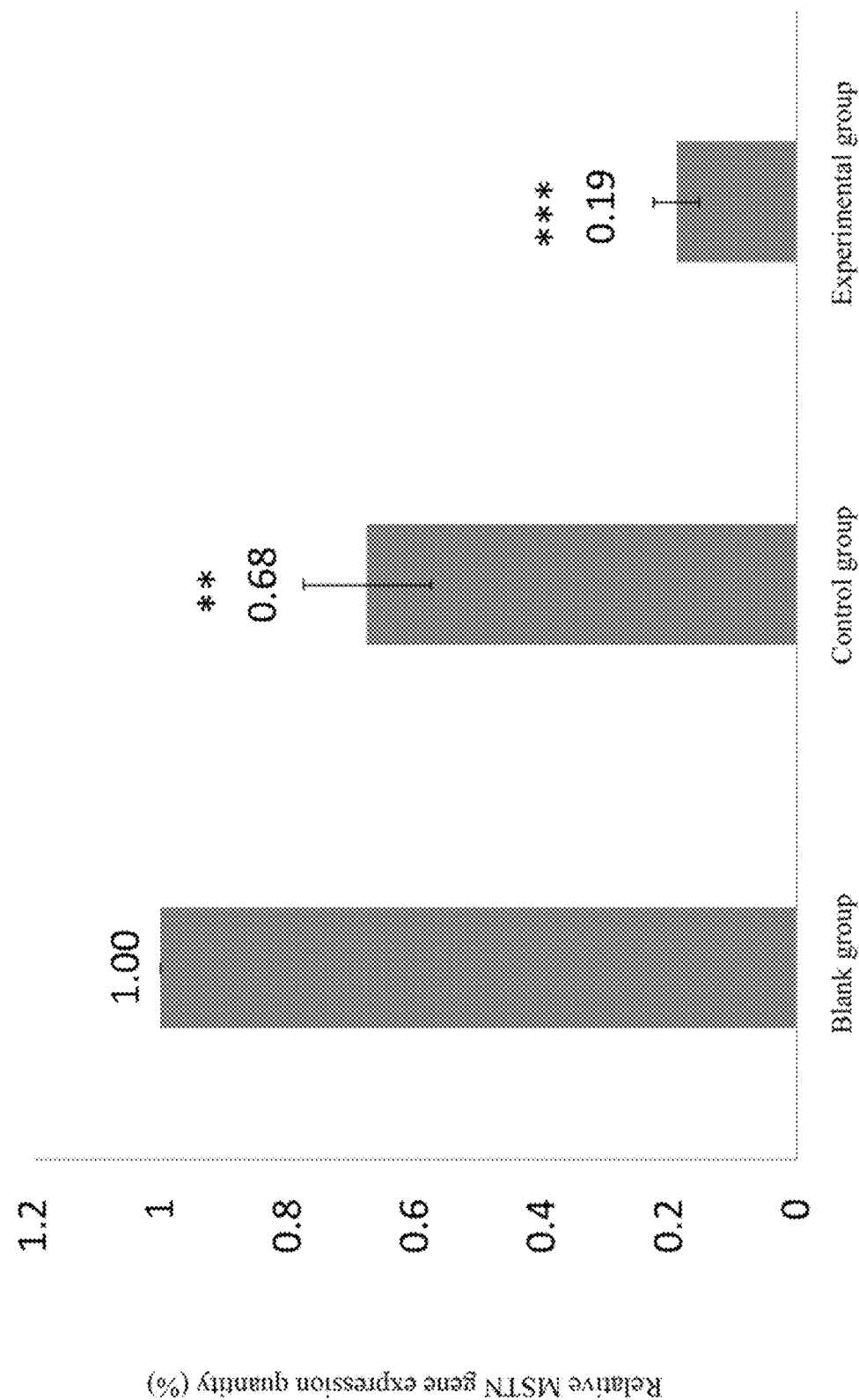
FIG. 5 is a result diagram of a test of Lactobacillus fermentum TCI757 in inhibiting myostatin.

See FIG. 5. When the expression quantity of the MSTN gene in the blank group was considered as 1, the expression quantity of the MSTN gene in the control group was 0.68, and the expression quantity of the MSTN gene in the experimental group was 0.19 with respect to the blank group, that was, the expression quantity of the MSTN gene in the experimental group was significantly reduced by 81% compared with the blank group. Even compared with a common inhibitor MRSD, the MSTN gene showed a better effect.

It should be particularly noted that what are shown in FIG. 5 are represented in relative magnification, i.e., the quantitative results of the experimental group are converted into the expression quantity with respect to the blank group with the quantitative results of the blank group being considered as 1. A standard deviation is calculated by using an STDEV formula of the Excel software, and is analyzed with a one-tailed student t-test in the Excel software for determining whether there is a statistically significant difference. In the figure, "*" represents that p value is less than 0.05 with respect to the blank group, "" represents that p value is less than 0.01 with respect to the blank group, and "*" represents that p value is less than 0.001 with respect to the blank group It can thus be seen that the expression quantity of a myostatin-related gene was obviously inhibited in a case where the Lactobacillus fermentum TCI757 was present in the muscle cell. That is, the Lactobacillus fermentum TCI757 effectively inhibited myostatin, thereby increasing muscle mass and preventing sarcopenia.

Example 7: Skeletal Muscle Cell Expansion Test 7-1. Test Materials and Equipment Description:

Cell Line: mouse skeletal muscle cells (hereinafter referred to as C2C12 cells; purchased from ATCC®CRL-1772™)

Medium: Minimum Essential Medium Alpha Medium cell medium (MEMAM, purchased from Gibco, USA) was used as a substrate, added with 20% of fetal bovine serum (purchased from Gibco, USA, Cat #10437-028), and 0.1% of penicillin-streptomycin (purchased from Gibco, USA).

Cell Expansion ELISA detection reagent kit (purchased from Roche, Model: 11647229001), including a cell fixation solution (FixDenat) and anti-BrdU-POD working solution (Bromodeoxyuridine BrdU, also known as an antibody conjugate).

7-2. Test Flows:

Here, the TCI757 sample cultivated in Example 2 was taken as a test sample. Whether the number of the cells was increased after the differentiated skeletal muscle cells underwent test sample treatment was detected Here, the experiment was conducted in three replicates.

A 24-well culture plate was taken, 5000 C2C12 cells were inoculated into each well of a 96-well plate, and the culture plate was put in a carbon dioxide incubator for culture at 37° C. for 2 h.

Then, the C2C12 cells were divided into two groups: a blank group and an experimental group. 100 μL of a sample to be tested and 10 μL of BrdU were added into each well in the experimental group, and only 10 μL of BrdU was added in the blank group without adding the test sample. Culture was performed for 24 h to obtain a medium of each group.

After the supernatant of the medium of each group was removed, 200 μL of cell fixation solution was added, and was treated at room temperature for 30 min.

After the cell fixation solution was removed, washing was performed once with 1×pbs. Subsequently, the anti-BrdU-POD working solution added into each well was treated at room temperature for 90 min.

Afterwards, the anti-BrdU-POD working solution was removed, thorough rinsing was performed three times with 200 to 300 μL of washing solution. Then, the washing solution was removed and 100 μL of substrate solution was added and was treated at room temperature for 15 min.

Subsequently, 25 μL of 1M $H_2SO_4$ was added into each well and was treated for 10 min, and then was vibrated on a 300 rpm vibrator for 1 min.

Figure 6:
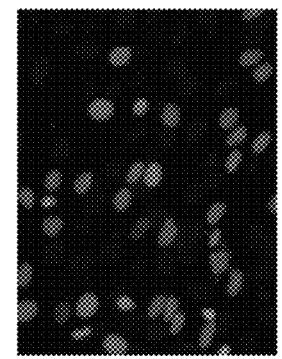
FIG. 6 is a cell state diagram of a test of Lactobacillus fermentum TCI757 in promoting skeletal muscle cell expansion.

Finally, pictures were taken under the microscope, as shown in FIG. 6, and the absorbance value (OD450 nm) of each well was read with the ELISA reader at a wavelength of 450 nm. When the cell number of the blank group was 100%, the cell number of the experimental group was converted, after comparative conversion of the absorbance values and multiplication by a dilution fold, as shown in FIG. 7.

Figure 7:
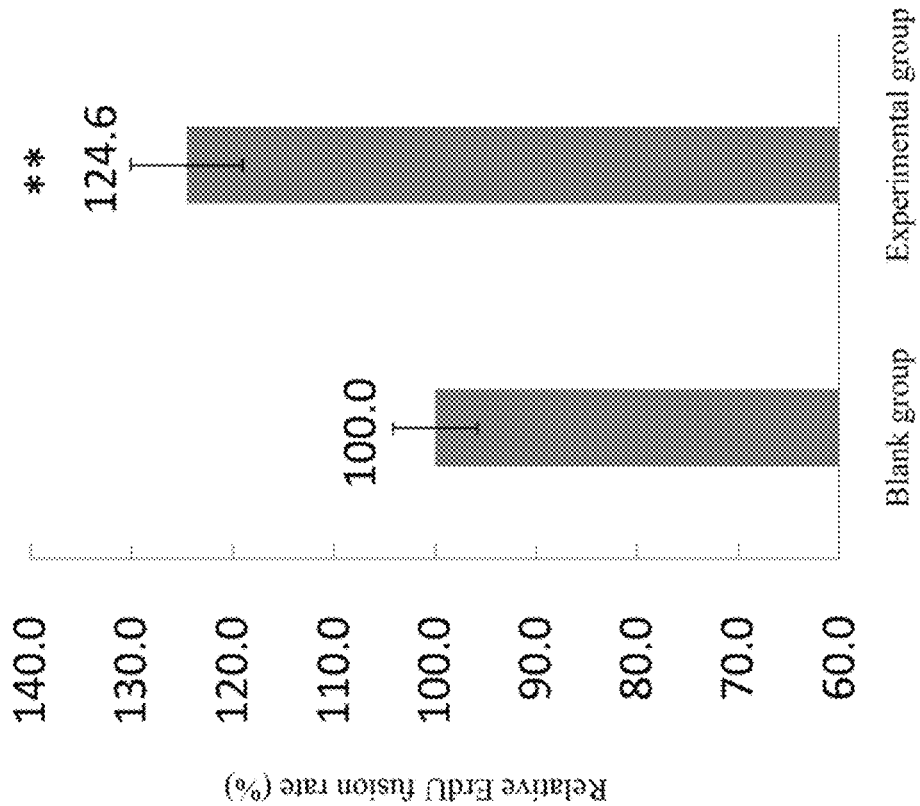
FIG. 7 is a result diagram of a test of Lactobacillus fermentum TCI757 in promoting skeletal muscle cell expansion.

7-3. Test Result:

A student t-test was performed on the obtained results by using Excel software, so as to determine that there was a statistically significant difference between the two sample populations, as shown in FIG. 7 (in the figure, "*" represents that p value is less than 0.05, "" represents that p value is less than 0.01, and "*" represents that p value is less than 0.001. The more the "*", the significant the statistical difference).

See FIG. 6. In the figure, blue light spots are cell nuclei, and green light spot is newly expanded cell nuclei. Compared with the blank group, there were more blue or green light spots in the experimental group, especially the number of green light spots was increased more significantly.

See FIG. 7. Compared with the blank group (that was, its relative cell number was regarded as 100%), the relative skeletal muscle number of the experimental group was 124.6%. In other words, the relative skeletal muscle number of the experimental group was increased by nearly 25% with respect to the blank group. It can thus be seen that the Lactobacillus fermentum TCI757 effectively promoted skeletal muscle cell expansion, and showed a potential of gaining muscle.

Example 8: Human Body Test 8-1. Sample:

Capsules prepared by the Lactobacillus fermentum TCI757 prepared in Example 2 contained 100 mg of bacterial powder. Here, the bacteria powder was prepared by adding 2.2% (w/w) of trehalose, 4.6% (w/w) of lactose and 10% (w/w) of skimmed milk powder into the Lactobacillus fermentum TCI757 bacterial solution prepared in Example 2, uniformly mixing, freezing and drying, and then grinding into powder.

8-2. Subject:

10 subjects. All the subjects were 20 years old or above and wanted to reduce body fat and increase muscle mass. The average weight of the 10 subjects was 70.88 kg and the average body fat was 28.35%.

8-3. Test Items:

body weight change, body fat weight, body fat rate, visceral fat area and palm grip strength.

8-4. Test Mode:

The 10 subjects were allowed to take 100 mg of capsules prepared from the Lactobacillus fermentum TCI757 daily for eight weeks. Measurement was performed before intake (i.e. week 0, also known as the control group) and eight weeks after intaking (i.e. week 8, also known as the experimental group) respectively.

The body weight (kg), the body fat weight (kg), the body fat rate (%) and the visceral fat area ($cm^2$) of the subjects were measured with a body composition analyzer (Model: InBody 770).

The grip strength (kg) of the subject was measured with a hand dynamometer (Model: CAMRY EH101 electronic hand dynamometer).

Figures 8, 9:
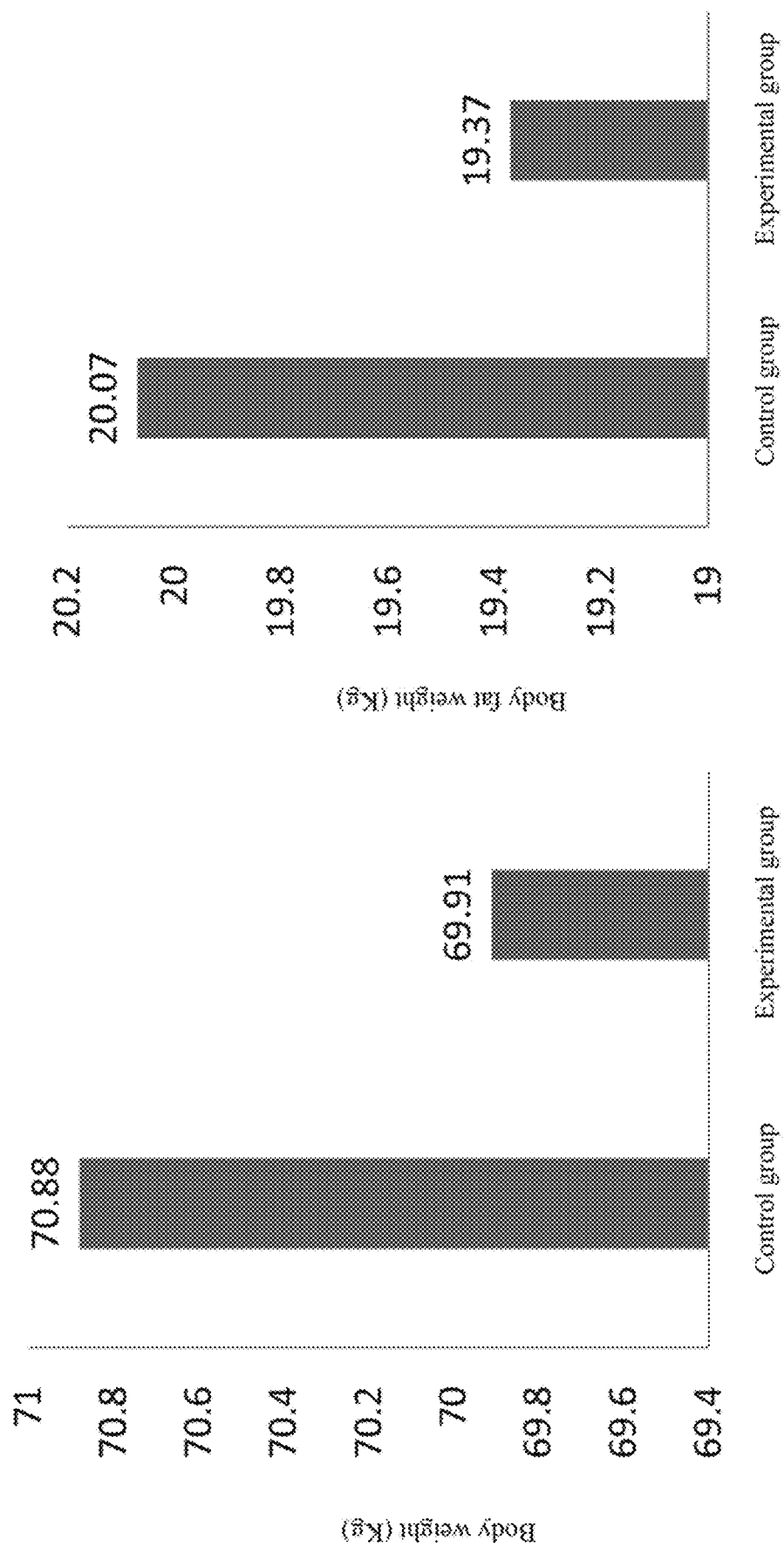
FIG. 8 is a weight change result diagram of a human experiment of Lactobacillus fermentum TCI757.
FIG. 9 is a body fat weight change result diagram of a human experiment of Lactobacillus fermentum TCI757.

8-5. Test Result:

See FIG. 8. After the 10 subjects took 100 mg of the Lactobacillus fermentum TCI757 daily for eight weeks, the average body weight decreased from 70.88 kg (week 0) to 69.91 kg (week 8) in a case where daily diet and exercise were maintained. After taking the Lactobacillus fermentum TCI757 of the present invention for only 8 weeks, the average weight difference between before and after taking reached 0.97 kg. That is, the body weight could be effectively reduced by taking 100 mg of the Lactobacillus fermentum TCI757 daily.

See FIG. 9. After the 10 subjects took 100 mg of the Lactobacillus fermentum TCI757 daily for eight weeks, the average body fat weight decreased from 20.07 kg (week 0) to 19.37 kg (week 8) in a case where daily diet and exercise were maintained. After taking the Lactobacillus fermentum TCI757 of the present invention for only 8 weeks, the average body fat weight difference between before and after taking reached 0.7 kg. That is, the body fat weight could be effectively reduced by taking 100 mg of the Lactobacillus fermentum TCI757 daily.

It can be seen from the above two types of data that the average body weight of the subjects decreases by 0.97 kg, and the average body fat weight decreases by 0.7 kg, from which, it can be seen that more than 72% of the body weight decreased is fat weight, not muscle weight, thereby significantly achieving an effect of gaining muscle and reducing fat.

Figures 10, 11:
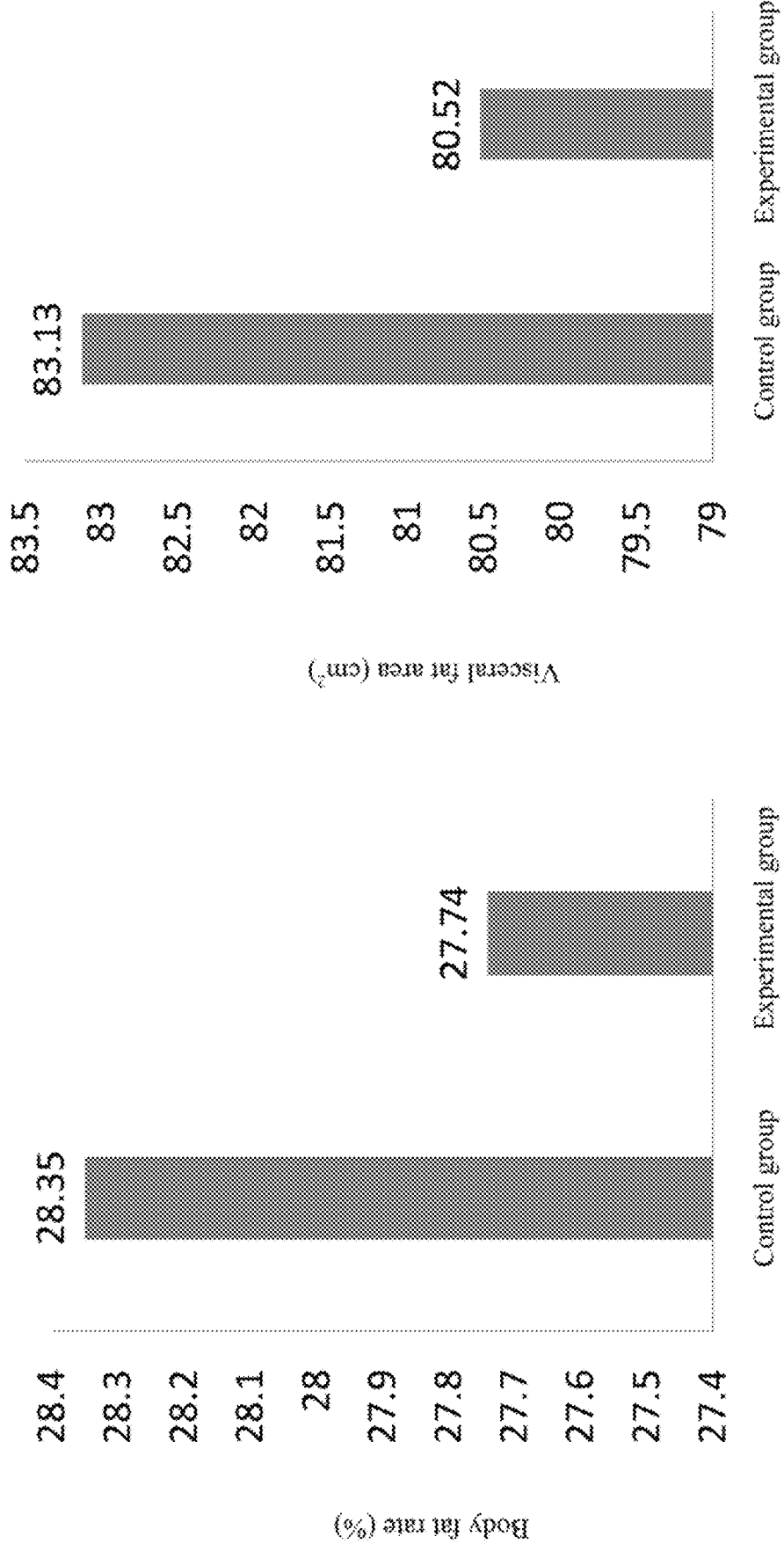
FIG. 10 is a body fat rate change result diagram of a human experiment of Lactobacillus fermentum TCI757.
FIG. 11 is a visceral fat area change result diagram of a human experiment of Lactobacillus fermentum TCI757.

See FIG. 10. After the 10 subjects took 100 mg of the Lactobacillus fermentum TCI757 daily for eight weeks, the average body fat rate decreased from 28.35% (week 0) to 27.74% (week 8) in a case where daily diet and exercise were maintained. After taking the Lactobacillus fermentum TCI757 of the present invention for only 8 weeks, the average body fat rate before and after taking was reduced by 0.61%. That is, the body fat rate could be effectively reduced by taking 100 mg of the Lactobacillus fermentum TCI757 daily.

See FIG. 11. After the 10 subjects took 100 mg of the Lactobacillus fermentum TCI757 daily for eight weeks, the average visceral fat area decreased from 83.13 $cm^2$ (week 0) to 80.52 $cm^2$ (week 8) in a case where daily diet and exercise were maintained. After taking the Lactobacillus fermentum TCI757 of the present invention for only 8 weeks, the average visceral fat area before and after taking was reduced by 2.61 $cm^2$. That is, the visceral fat area could be effectively reduced by taking 100 mg of the Lactobacillus fermentum TCI757 daily.

Figure 12:
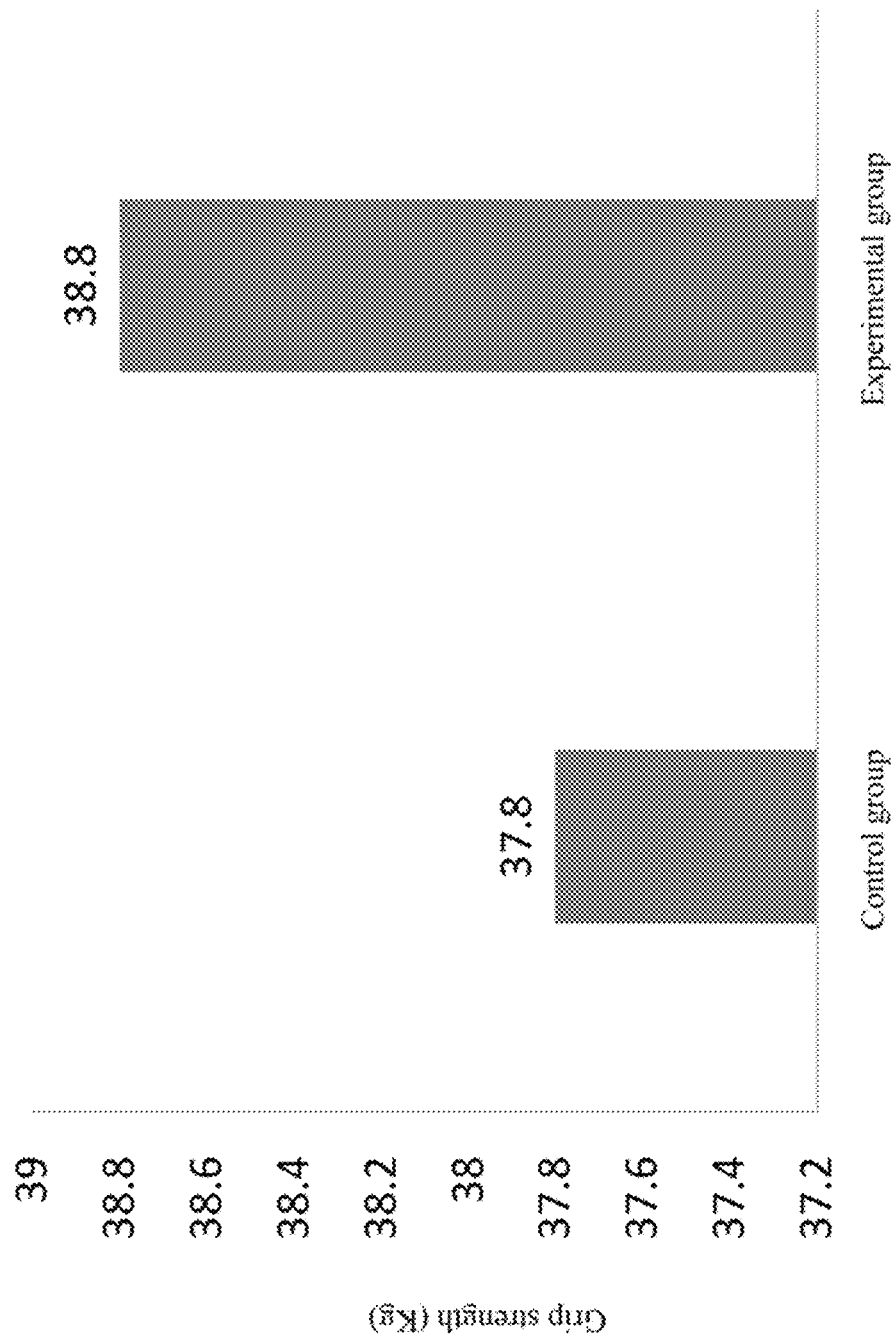
FIG. 12 a grip strength change result diagram of a human experiment of Lactobacillus fermentum TCI757.

See FIG. 12. After the 10 subjects took 100 mg of the Lactobacillus fermentum TC1757 daily for eight weeks, the average palm grip strength increased from 37.8 kg (week 0) to 38.8 kg (week 8) in a case where daily diet and exercise were maintained. After taking the Lactobacillus fermentum TCI757 of the present invention for only 8 weeks, the average palm grip strength before and after taking was increased by 1 kg. That is, the grip strength can be effectively increased and the muscle strength could be improved by taking 100 mg of the Lactobacillus fermentum TC1757 daily.

It can thus be seen that the taking of the Lactobacillus fermentum TCI757 and metabolites thereof can inhibit myostatin, promote skeletal muscle cell expansion, promote secretion of irisin, increase secretion of adiponectin, inhibit fat accumulation, reduce body weight, reduce body fat weight, reduce visceral fat area, and improve grip strength, thereby achieving the effect of gaining muscle and reducing fat.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

of the Lactobacillus fermentum TC1757 is DSM 33914, and the Lactobacillus fermentum TC1757 comprises a full length nucleotide sequence as set forth in SEQ ID NO: 1.

2. The method according to claim 1, wherein the Lactobacillus fermentum TCI757 promotes skeletal muscle cell expansion.

3. The method according to claim 1, wherein the Lactobacillus fermentum TCI757 promotes grip strength.

4. The method according to claim 1, wherein the effective dose of the Lactobacillus fermentum TCI757 is $10^8$ CFU/day.

5. A method of using Lactobacillus fermentum TC1757 for promoting secretion of irisin in a subject in need thereof, comprising administering to the subject an effective dose of the Lactobacillus fermentum TC1757, wherein an accession number of the Lactobacillus fermentum TC1757 is DSM 33914, and the Lactobacillus fermentum TC1757 comprises a full length nucleotide sequence as set forth in SEQ ID NO: 1.

What is claimed is:

1. A method of using Lactobacillus fermentum TC1757 for gaining muscle by promoting irisin secretion and inhibiting myostatin in a subject in need thereof, comprising administering to the subject an effective dose of the Lactobacillus fermentum TC1757, wherein an accession number 6. The method according to claim 5, wherein the Lactobacillus fermentum TCI757 promotes skeletal muscle expansion.

7. A method of using Lactobacillus fermentum TC1757 for decreasing visceral fat in a subject in need thereof, comprising administering to the subject an effective dose of the Lactobacillus fermentum TC1757, wherein an accession number of the Lactobacillus fermentum TC1757 is DSM 33914, and the Lactobacillus fermentum TC1757 comprises a full length nucleotide sequence as set forth in SEQ ID NO: 1.

8. The method according to claim 7, wherein the Lactobacillus fermentum TCI757 promotes secretion of adiponectin.

9. The method according to claim 7, wherein the Lactobacillus fermentum TCI757 transforms white fat into brown adipocytes.

10. The method according to claim 7, wherein the Lactobacillus fermentum TCI757 accelerates heat-production metabolism of fat.

11. The method according to claim 7, wherein the Lactobacillus fermentum TCI757 inhibits fat accumulation.

12. The method according to claim 7, wherein the Lactobacillus fermentum TCI757 reduces body weight.

13. The method according to claim 7, wherein the Lactobacillus fermentum TCI757 reduces body fat weight.

* * * * *

SEQUENCE LISTING

```
Sequence total quantity: 3
SEQ ID NO: 1            moltype = DNA  length = 1146
FEATURE                 Location/Qualifiers
source                  1..1146
                        mol_type = genomic DNA
                        organism = Lactobacillus fermentum
SEQUENCE: 1
ccaaaaaatc tgtgcacctt aggcggctgg ctcctaaaag gttacccgac cgactttggg  60
tgttacaaac tctcatggtg tgacggcgg tgtgtacaag gcccgggaac gtattcaccg  120
cggcatgctg atccgcgatt actagcgatt ccgacttcgt gcaggcgagt tgcagcctgc  180
agtccgaact gagaacggtt ttaagagatt tgcttgccct cgcgagttcg cgactcgttg  240
taccgtccat tgtagcacgt gtgtagccca ggtcataagg ggcatgatga tctgacgtcg  300
tccccacctt cctccggttt gtcaccggca gtctcactag agtgcccaac ttaatgctgg  360
caactagtaa caagggttgc gctcgttgcg ggacttaacc caacatctca cgacacgagc  420
tgacgacgac catgcaccac ctgtcattgc gttcccgaag gaaacgccct atctctaggg  480
ttggcgcaag atgtcaagac ctggtaaggt tcttcgcgta gcttcgaatt aaaccacatg  540
ctccaccgct tgtgcgggcc cccgtcaatt cctttgagtt tcaaccttgc ggtcgtactc  600
cccaggcgga gtgcttaatg cgttagctcc ggcactgaag ggcggaaacc ctccaacacc  660
tagcactcat cgtttacggc atggactacc agggtatcta atcctgttcg ctacccatgc  720
tttcgagtct cagcgtcagt tgcagaccag gtagccgcct tcgccactgg tgttcttcca  780
tatatctacg cattccaccg ctacacatgg agttccacta ccctcttctg cactcaagtt  840
atccagtttc cgatgcactt ctccggttaa gccgaaggct ttcacatcag acttagaaaa  900
ccgcctgcac tctctttacg cccaataaat ccggataacg cttgccacct acgtattacc  960
gcggctgctg gcacgtagtt agccgtgact ttctggttaa ataccgtcaa cgtatgaaca  1020
gttactctca tacgtgttct tctttacaca gagctttacg agcgaaaccc ttcttcactc  1080
acgcggtgtt gctccatcag gctgcgccat tgtggaagat cctacggtcc ccccgcagc  1140
gagaga                                                             1146

SEQ ID NO: 2            moltype = DNA  length = 19
FEATURE                 Location/Qualifiers
source                  1..19
                        mol_type = other DNA
                        organism = synthetic construct
SEQUENCE: 2
ttccggttcc tttcccctt                                                19

SEQ ID NO: 3            moltype = DNA  length = 20
FEATURE                 Location/Qualifiers
source                  1..20
                        mol_type = other DNA
                        organism = synthetic construct
SEQUENCE: 3
tctgcagctt gtgttgctct                                               20
```